United States Patent [19]

Pike

[11] Patent Number: 4,655,215
[45] Date of Patent: Apr. 7, 1987

[54] HAND CONTROL FOR ELECTROSURGICAL ELECTRODES

[76] Inventor: Harold Pike, 10 Hier La., Castle Rock, Colo. 80104

[21] Appl. No.: 712,271

[22] Filed: Mar. 15, 1985

[51] Int. Cl.$^4$ .............................................. A61B 17/36
[52] U.S. Cl. ............................ 128/303.14; 128/303.17
[58] Field of Search ........... 128/303.1, 303.14, 303.13, 128/303.17; 200/1 R, 1 A, 43.16, 43.17, 157, 334, 339

[56] References Cited

U.S. PATENT DOCUMENTS

| | | | |
|---|---|---|---|
| 1,639,996 | 8/1927 | Groff | 128/303.14 |
| 2,012,316 | 8/1935 | Miles | 128/303.14 |
| 2,717,614 | 12/1959 | Cabii et al. | 128/303.1 |
| 2,735,910 | 2/1956 | Dautry | 200/1 A |
| 3,555,228 | 1/1971 | Ohno | 200/1 A |
| 3,648,001 | 3/1972 | Anderson et al. | 128/303.14 |
| 3,720,896 | 3/1973 | Beierlein | 128/303.13 |
| 3,801,766 | 4/1974 | Morrison, Jr. | 128/303.14 |
| 3,823,291 | 7/1974 | Milcoy | 200/157 |
| 4,071,028 | 1/1928 | Perkins | 128/303.17 |
| 4,078,569 | 3/1978 | Hoshi | 128/303.13 |
| 4,228,800 | 10/1980 | Degler, Jr. et al. | 128/303.14 |
| 4,427,006 | 1/1984 | Nottke | 128/303.17 |
| 4,443,935 | 4/1984 | Zamba et al. | 128/303.14 |
| 4,463,759 | 8/1984 | Garito et al. | 128/303.14 |
| 4,492,832 | 1/1985 | Taylor | 128/303.13 |
| 4,545,375 | 10/1985 | Clive | 128/303.17 |

Primary Examiner—Edward M. Coven
Assistant Examiner—Max F. Hindenburg
Attorney, Agent, or Firm—Fields, Lewis, Pittenger & Rost

[57] ABSTRACT

A hand control for electrosurgical electrodes with the rocker arm current mode activating switch located near the front of the device. The activating switch allows a choice of coagulating current mode, cutting current mode, or neutral (no current mode). A three-position slide-locking mechanism allows the switch to be operated in one of three states: (1) complete freedom of choice of mode, (2) coagulating mode only, or (3) neutral (safety). A top-bottom symmetry and a sharp blade permit the device to be locked in the neutral position, inverted, and used as a conventional scalpel.

8 Claims, 11 Drawing Figures

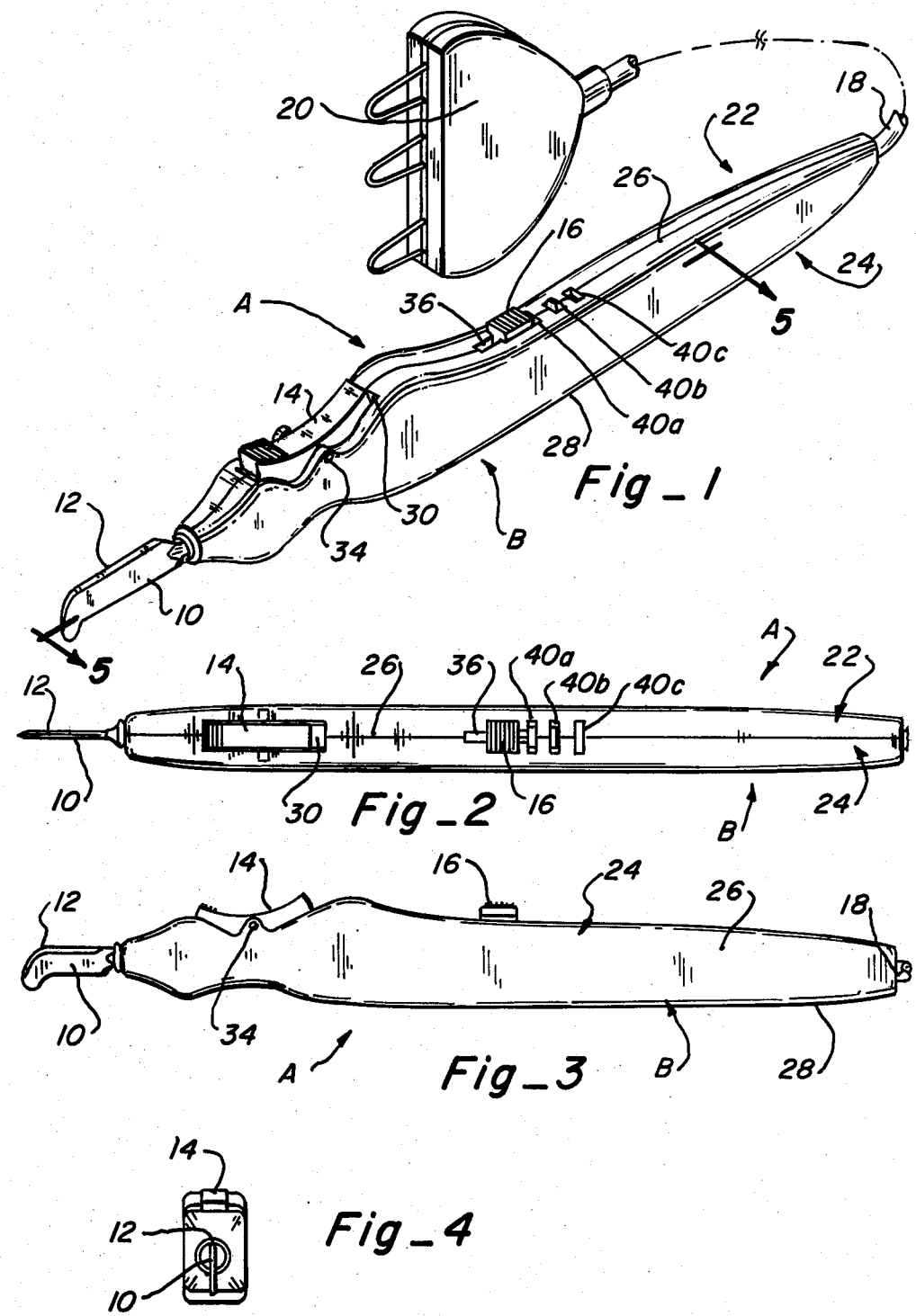

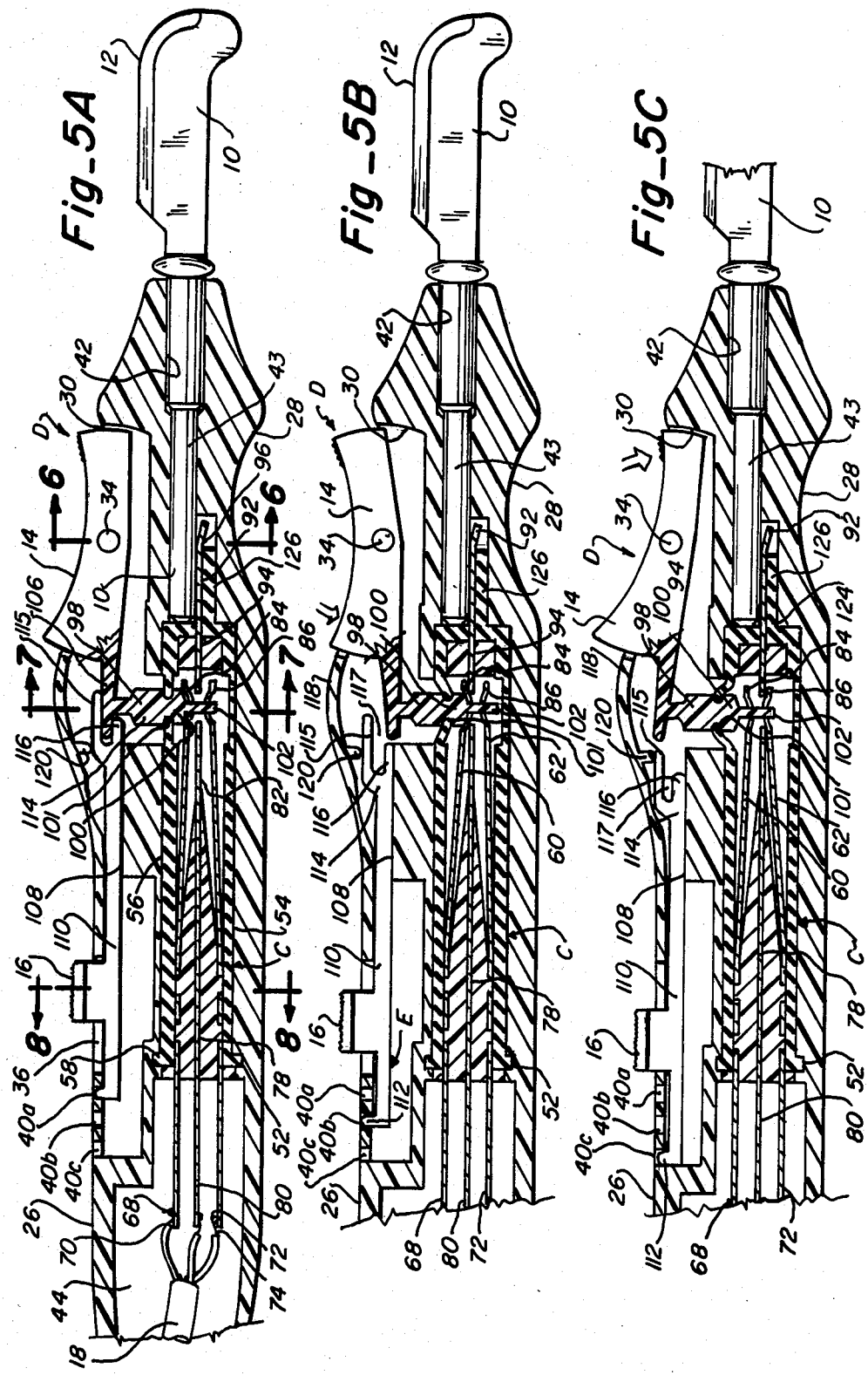

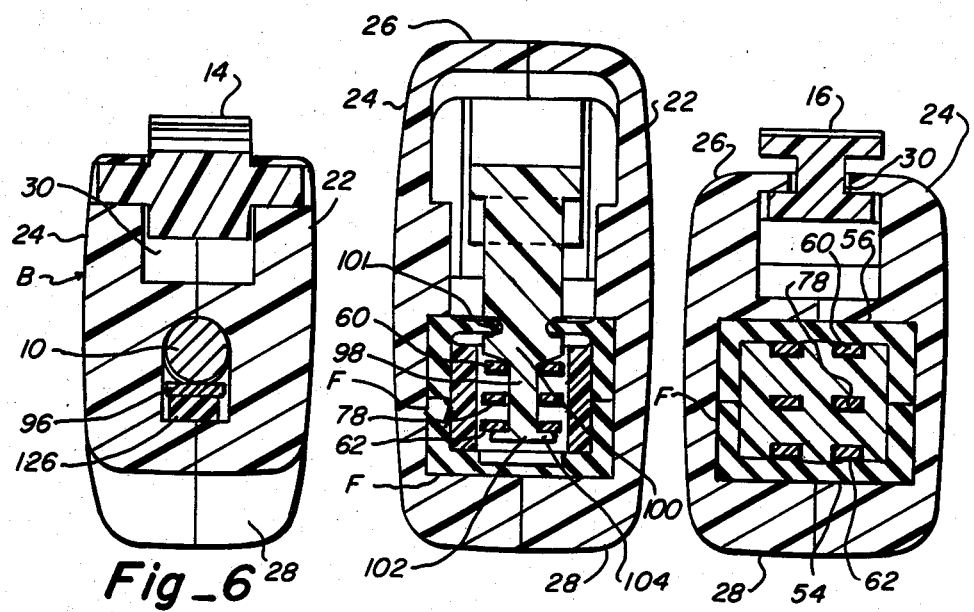
Fig_6   Fig_7   Fig_8
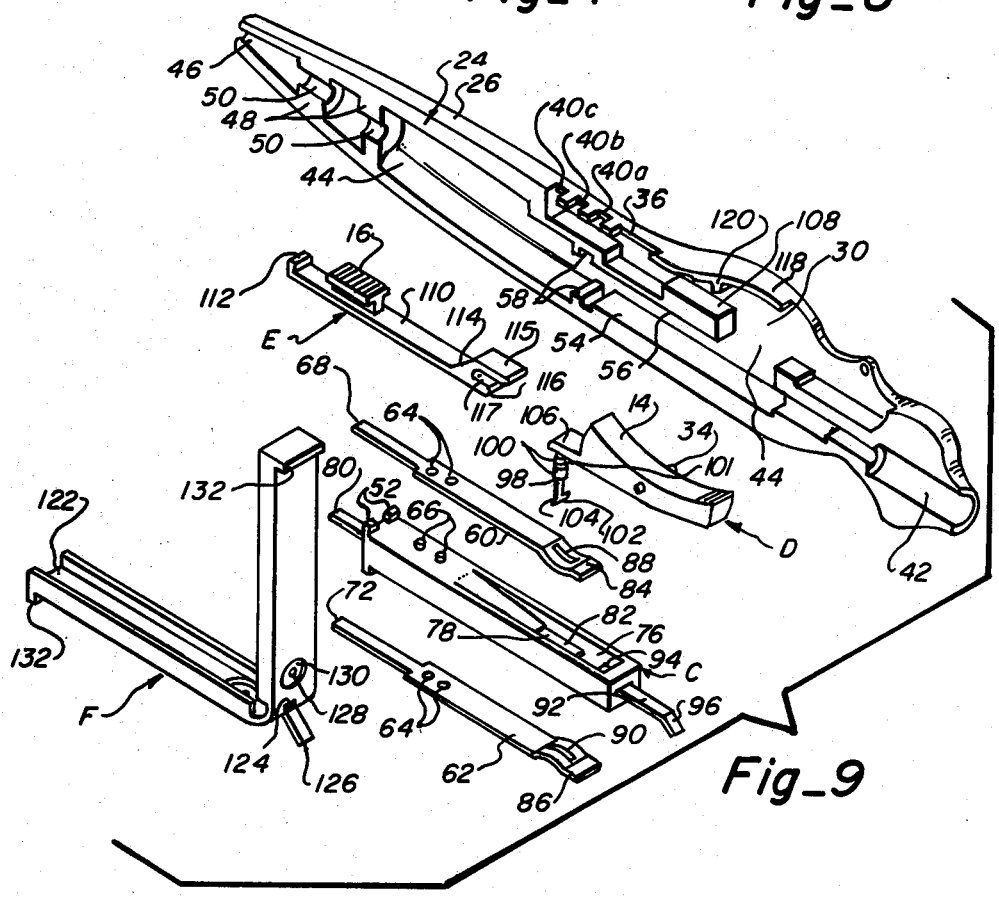
Fig_9

HAND CONTROL FOR ELECTROSURGICAL ELECTRODES

TECHNICAL FIELD

The present invention relates to surgical instruments and, more particularly, to an improved hand control for electrosurgical electrodes for holding a scapel electrode capable of selectively cutting tissue and/or coagulating blood.

BACKGROUND ART

Medical electronic apparatus has been employed for many years for many types of diagnosis and treatment. One field in which there has been considerable growth recently is electrosurgery, in which a suitable generator provides a high frequency, high voltage current which is transmitted to a small surgical electrode having a thin knife-like tip to be applied to a patient. The patient sits or lies on a patient plate and is grounded thereto, with the plate being connected by a further conductor back to the generator. The relatively extremely small area of contact by the electrode with the patient provides an intense current in a highly localized area, producing a cutting action. The current passes through the patient's body to the patient plate where the area of contact is so great that no burning effect occurs.

For cutting purposes, the generator is activated to produce a continuous sine wave signal. However, the same instrument may be used to apply to the wound after cutting in order to produce coagulation. For this purpose the generator may be selectively activated to produce a pulsing signal which produces the desired results. Switching means are available for the operator to selectively control an activating means for causing the generator to produce the desired type of current.

In the operating room, a surgeon would like to use the electrosurgical device in a fashion similar to that in which he uses a standard sharp scalpel. The surgeon typically grips the scalpel like a pencil with index finger guiding and hear the cutting tip for precise control. Currently available electrosurgical hand instruments, called "pencils", are not readily gripped this way, because the mode switches are positioned far from the cutting tip, toward the rear of the instrument. This requires the surgeon to grip the pencil far back on the handle in order to have the index finger positioned to activate the mode buttons, resulting in awkward feel and loss of precise control. An additional disadvantage of electrosurgical pencils is the possibility of inadvertent activations of the mode switches by pressures being applied to the unit. If this occurs when the tip is in contact with the patient or with conductive items, a serious burn can result. Another drawback to the use of electrosurgical pencils has been that many surgeons still desire to use a sharp scalpel for incision-making, with coagulation being achieved by the electrosurgical pencil. This requires the surgeon to continually switch from one instrument to the other.

Electrosurgical pencils with a rocker switch for selection of mode of operation are disclosed in U.S. Pat. No. 4,228,800 to Degler, Jr., et al, U.S. Pat. No. 3,648,001 to Anderson, et al, U.S. Pat. No. 4,443,935 to Zamba, et al, and U.S. Pat. No. 3,801,766 to Morrison, Jr. As is typical among such devices, the pencil in each is connected to an electrosurgical generating apparatus by a cable comprising three conductors: a first signal line, a second signal line, and a common line which serves not only to return the selected control signal to the generator, but also to deliver current to the scalpel electrode. Thus, all three conductors are maintained at high voltage, with the control signal conductors differing in voltage slightly from the common conductor so that a relatively small current will serve to select the mode of operation desired.

U.S. Pat. No. 3,720,896 to Beierlein discloses a magnetic slide switch with three positions, and appears to provide electrical isolation when in the center position. U.S. Pat. No. 4,463,759 to Garito, et al. also provides electrical isolation.

DISCLOSURE OF THE INVENTION

The construction of the present invention overcomes the difficulties mentioned above, and provides a device which is easy to use, safe, and versatile. An electrosurgical hand control electrode holder for holding a scalpel electrode capable of selectively cutting tissue and/or coagulating blood is disclosed. The type of cutting or coagulating current desired is selected by the setting of a switch which activates the proper circuitry thus transferring the desired mode of current to the electrode forming the blade of the surgical instrument. Thus, the instrument can perform selected electrosurgical functions without the need of utilizing separate cutting tips or different instruments.

The apparatus utilizes a rocker arm activating switch having a cantilevered contact arm for making electrical contact with the wires. This novel cantilvered construction allows the switch to be placed close to the blade, where it is more easily used by the surgeon, as compared to a switch located further back from the blade.

In addition, a three-position slide-locking mechansim for the activating switch is provided. With the slide-locking mechanism in the rear position, the activating switch can be freely moved to any mode position. With the slide-locking mechanism in the center position, the activating switch cannot be placed in the cutting mode position. This allows the device to be used exclusively for its coagulating function, without the possibility of inadvertent activation of the cutting mode. With the slide-locking mechanism in the forward position, the activating switch cannot be moved at all, and no current can reach the electrosurgical blade, thus protecting the patient from inadvertent burns caused by accidental movement of the activating switch.

Furthermore, the hand control housing has a top surface and a bottom surface substantially identical in shape, and an electrosurgical blade with a sharp edge up and with the electrosurgical cutting hook down. This allows the surgeon to use the device as an electrosurgical tool in the upright position, or as a conventional scalpel by locking the mode control in the neutral position, inverting the device, and using the sharp edge as a normal sharp scalpel.

Various other advantages and features of novelty will become apparent as the description proceeds in conjunction with the accompanying drawings.

BRIEF DESCRIPTION OF THE DRAWINGS

FIG. 1 is a perspective view of the electrosurgical instrument of this invention;

FIG. 2 is a top plan view of the electrosurgical instrument of FIG. 1;

FIG. 3 is a side elevational view of the electrosurgical instrument of FIG. 1;

FIG. 4 is a front elevational view of the electrosurgical instrument of FIG. 1;

FIG. 5A is a longitudinal cross-sectional view of the electrosurgical instrument taken along line 5—5 of FIG. 1, showing the slide-locking mechanism in the forward position;

FIG. 5B is a longitudinal cross-sectional view similar to FIG. 5A, but showing the side-locking mechanism in the middle position;

FIG. 5C is a longitudinal cross-sectional view similar to FIG. 5A and 5B, but showing the slide-locking mechanism in the rear position;

FIG. 6 is a vertical cross-sectional view of the electrosurgical instrument, taken along line 6—6 of FIG. 5A;

FIG. 7 is a vertical cross-sectional view of the electrosurgical instrument, taken along line 7—7 of FIG. 5A;

FIG. 8 is a vertical cross-sectional view of the electrosurgical instrument, taken along line 8—8 of FIG. 5A; and FIG. 9 is an exploded perspective view of the electrosurgical instrument showing the arrangement of the various components thereof.

DESCRIPTION OF THE PREFERRED EMBODIMENT

In accordance with this invention, an electrosurgical hand instrument A is illustrated in FIGS. 1-9 of the drawings. Turning to FIG. 1, the instrument comprises a housing B, an electrosurgical blade 10 extending from the distal end of the housing B and having one sharp cutting edge 12, a rocker arm control switch 14 and a slide-locking thumb release 16, both protruding from the surface of the housing B, a cable 18 extending from the proximal end of the housing B, and a connector plug 20 attached to an end of the cable 18 remote from the housing B. The connector plug 20 is advantageously a three-contact asymmetric connector, so as to prevent inadvertent reversed installation of connector 20 to a current supply electrosurgical generator for the instrument A.

Any conventional dual-mode current supply or electrosurgical generator (not shown), as it is well known in the art and purchasable from several manufactures, may be utilized in conjunction with the present electrosurgical instrument A. As is also well-known in the art, the control circuit established through the switch 14, cable 18 and connector 20 utilizes two control signal conductors and a common conductor which may be connected alternatively to either of the two control signal conductors by manipulation of the switch 14. Simultaneously, the common conductor is also utilized to deliver current to a standard electrosurgical blade 10 which completes a current circuit through the body of the patient and a return electrode of the patient and a return electrode of substantial area attached to the patient.

The housing B is also illustrated in FIGS. 2 and 3. Housing B comprises an injection molded right half 22 and left half 24, both preferably constructed of high impact plastic, which are riveted together to form a unitary housing B, having a top surface 26 and a bottom surface 28. Top surface 26 and bottom surface 28 are substantially the same shape, allowing the pencil to be used interchangeably in either an upright position (to up) or an inverted position (top down).

A portion of the top surface 26 of the housing B defines a rectangularly shaped switch seat or recess 30 which communicates with the interior of the housing B. Control switch 14 rests in the switch seat 30, and rotates on a fulcrum or rocker pin 34 which is preferably integrally molded with the switch. A portion of the top surface 26 of the housing B further defines a rectangularly shaped slide-locking thumb release groove 36 which communicates with the interior of the housing B, and three rectangular locking notches 40a, 40b, 40c, which are also in communication with the interior of the housing B. Slide-locking thumb release 16 slides in as in groove 36, and is locked into position by a locking member (discussed in detail later) having a locking flange which fits securely into one of notches 40a, 40b or 40c as the slide-locking thumb release 16 is moved forward and backward.

The internal structure of housing B is illustrated in FIGS. 5A, 5B, and 5C, and FIG. 9. Both halves 22 and 24 together define a proximal socket bore 42 for removable installation of blade 10, an interior chamber 44 adapted to hold a conductor member and electrical contacts and wires, as well as a proximal aperture 46, best seen in FIG. 9, for cable 18. Adjacent proximal aperture 46 in the rear of the housing, a plurality of support walls 48 are formed which, when both halves are assembled together extend across chamber 44, define a cable bore 50 for location of cable 18.

A contact support member C having a plurality of retaining shoulders 52 at its distal end is located adjacent to a rocker arm mechansim D in chamber 44. The contact support member C is supported between interior chamber surfaces 54 and 56, and is held in place by retaining notches 58 in interior surfaces 54 and 56. Cutting signal spring contact 62 and coagulating signal spring contact 60 are attached to and extend lengthwise along contact support member C. The spring contacts 60 and 62 define a plurality of placement holes 64 through which pass placement pins 66, thereby securing spring contacts 60 and 62 to contact support member C. Spring contacts 60 and 62 may be made from any suitable metallic material which can carry current to the blade 10, and maintain a springiness to force rocker switch mechanism D to the illustrated neutral position when not in use. Spring contact 60 has a proximal end 68 having a coagulating signal conducting wire 70 welded thereto, forming an electrically conductive connection. Spring contact 62 also has a proximal end 72, in like manner having a cutting signal conducting wire 74 welded thereto, forming an electrically conductive connection.

Contact support member C further defines a vertical contact channel 76 near its distal end. A common current conductor blade 78 runs lengthwise axially through the contact support member C, having a proximal end 80 extending rearward from the proximal end of the contact support member C, and a distal end 82 terminating in channel 76. Spring contacts 60 and 62 have distal ends 84 and 86 respectively, overlapping the distal end 82 of common current conductor blade 78, and terminating in channel 76. Said distal ends 84 and 86 define rectangular plunger slots 88 and 90, respectively.

An electrode current conductor blade 92 runs lengthwise axially through the distal end of contact support member C and has a proximal end 94 in contact channel 76, and a distal end 96 extending forward from the control support member C and terminating in socket bore 42, where it rests on the bottom surface of the socket bore 42 and makes contact with the stepped shaft 43 of electrosurgical blade 10.

Rocker arm switch mechanism D further includes a cantilevered plunger 98 extending downward from a locking shoulder 106 at the rear end of rocker arm 14. Plunger 98 has shoulders 100 on its upper portion defining insulation locking recess 101, and a T-shaped tip 102 having flanges 104 at its lower end.

When assembled, plunger 98 passes through plunger slots 88 and 90 in contact channel 76, with distal contact end 96 resting on plunger flanges 104 and with distal contact end 94 underneath and against plunger shoulder 100. This is also well illustrated in the front cross-sectional view of FIG. 7. When the plunger 98 is moved downward by pressure on the proximal end of control switch 14, the plunger shoulders 100 press downward on the distal end 84 of coagulating signal spring contact 60, forcing it into contact with the distal end 82 of common current conductor blade 78 and the proximal end 94 of electrode current conductor blade 92. This completes an electrical circuit through shaft 43 of the blade 10, delivering a coagulating current to the blade 10. When pressure is released from the control switch 14, spring pressure from spring contact 60 exerted on the plunger shoulders 100 causes the plunger to return to a neutral position where no electrical contact is made between blades 78 and 92 and spring contacts 60 and 62. In similar fashion, pressure on the distal portion of control switch 14 moves the plunger upward, causing the plunger tip flanges to pull upward on the distal end 86 of spring contact 62, forcing it into contact with the distal end 82 of common current conductor blade 78 and the proximal end 94 of electrode current conductor blade 92. This completes an electrical circuit through the blade 10, delivering a cutting current thereto. When the control switch 14 is released, spring pressure from spring contact 62 is exerted on the plunger tip flanges 104, causing the plunger to return to the neutral position as illustrated in FIG. 7.

A slide-locking member E is sandwiched between a locking mechanism support surface 108 and the upper surface of interior chamber 44, and is free to slide forward and backward therein. Slide-locking member E comprises a locking arm 110, a slide-locking flange 112 located at the distal end of locking arm 110, a slide-locking thumb release 16 located forward of the locking flange 112 and extending upward above the top surface 26 of the housing B through thumb release groove 36, and a forked locking shoulder 114 located at the distal end of the slide-locking member E and having an upper flange 115 and a shorter lower flange 116 together defining a locking recess 117. A convex slide-locking shoulder curve 118 in the top surface 26 of housing B provides space for the locking shoulder 114 to slide forward and backward within chamber 44. A locking shoulder restraining flange 120 abuts the top surface of locking shoulder 114, and prevents upward motion of shoulder 114 as the shoulder slides horizontally.

In operation, slide-locking mechanism E can be moved into three positions, each position affecting the operation of the control switch 14 differently. When thumb release 16 is moved backward so that locking flange 112 is inserted into rear locking notch 40c, rocker arm locking shoulder 106 is free to move vertically in either direction without coming in contact with forked locking shoulder 114, thus allowing the plunger 98 to move spring contacts 60 and 62 into either a coagulating or cutting mode electrical connection with common current conductor blade 78 and electrode current conductor blade 92. When thumb release 16 is positioned so that locking flange 112 is inserted into forward locking notch 40a, rocker arm locking shoulder 106 is inserted into locking recess 117 and is restrained from any vertical movement by upper flange 115 and lower flange 116, and spring contacts 60 and 62 are thus locked in the neutral position, unable to electrically connect with either conductor blade 78 or conductor blade 92. Thus, when the slide-locking member E is in this position, no current can reach the electrosurgical blade 10. When the thumb release 16 is moved forward so that locking flange 112 is inserted into center locking notch 40b, rocker arm locking shoulder 106 is restrained from moving upward a sufficient distance to complete the cutting mode circuit of spring contact 62, electrode current conductor blade 92 and common current conductor blade 78. This prevents the cutting mode from being activated while the slide-locking member E is so positioned.

A flexible insulation housing F fully encloses spring contacts 60 and 62 and contact support member C to prevent electrical shorting by moisture or otherwise. Housing F defines a housing channel 122 of substantially rectangular cross-section. Contacts 60 and 62 and contact support member C fit into half of the channel 122, and the other half of the housing F is folded back over the top of the contacts 60 and 62 and support member C to completely enclose them. Housing F has an electrode current blade housing aperture 124 through which electrode current blade 92 extends forward from the housing F. The housing F further has an insulating tongue 126, which is adjacent to and compressed by the under-side of blade 92 when the cutting blade 10 is inserted in socket bore 42 to provide a tight fit. Housing F has a plunger aperture 128, having a rim 130, in the upper surface of the aperture. Plunger 98 is inserted through aperture 128, and rim 130 fits into insulation locking recess 101, forming a tight seal which moves with the movement of the plunger 98. Housing F has insulation retaining flanges 132 at both ends, said flanges 132 fitting into retaining notches 58, thus holding the housing F and its contents in place.

From the foregoing, the advantages of this invention are readily apparent. A hand control for electrosurgical electrodes is provided which is easier to use due to the positioning of the current control switch toward the front of the device, where it is conveniently accessed by the surgeon without changing his usual manner of using a scalpel. In addition, the device is safer and more secure to use as a result of the three-position slide-locking mechanism, which allows either (1) complete freedom of choice of current mode, (2) coagulating current mode only, or (3) no current at all to the electrosurgical blade. Furthermore, the symmetrical design and the sharp blade, combined with the capability for locking the current activating mode in neutral, allow the surgeon to turn the device over and use it as a conventional scalpel.

The invention has been described in detail with particular reference to preferred embodiments thereof, but it will be understood that variations and modifications can be effected within the spirit and scope of the invention.

I claim:

1. A hand control for electrosurgical electrodes, comprising:
    an elongated housing for containing electrical wiring circuits and circuits-switching means, said housing having a top surface and a bottom surface and a proximal or rear end and a distal or front end, and defining a switch seat in its top surface adjacent its distal end;

an electrosurgical blade having a proximal end in said housing and a distal end extending from said distal end of said housing;

a rocker arm control switch for activating at least two electrosurgical current modes of said electrosurgical blade, said switch having a proximal end and a distal end and being pivotably mounted between said ends in said switch seat, directly above the said proximal end of said electrosurgical blade;

finger-engaging portions on said proximal and distal ends of said rocker arm control switch for pivoting said control switch in two opposite directions;

a cantilevered shoulder portion rigidly mounted on said proximal end of said rocker arm control switch and extending rearward within said housing beyond said proximal end of said electrosurgical blade; and circuit closing means having a plurality of circuit modes, said circuit closing means being transversely mounted within said housing, between said top and bottom surfaces, rearwardly of said proximal end of said electrosurgical blade and connected to and movable with said shoulder portion to selectively activate said circuits.

2. A hand control for electrosurgical electrodes, comprising:

an elongated housing for containing electrical wiring and circuit-switching means, said housing having a top surface and a bottom surface and a proximal or rear end and a distal or front end, and defining a switch seat in its top surface adjacent its distal end;

an electrosurgical blade having a proximal end in said housing and a distal end extending from said distal end of said housing;

a rocker arm control switch for activating at least two electrosurgical current modes of said electrosurgical blade, said switch having a proximal end and a distal end and being pivotably mounted in said switch seat, directly above the proximal end of said electrosurgical blade;

finger-engaging portions on the proximal and distal ends of said rocker arm control switch for pivoting said control switch in two opposite directions;

a cantilevered shoulder portion on said rocker arm control switch, said shoulder portion extending rearward within said housing from said control switch;

circuit closing means having a plurality of circuit modes, said circuit closing means being activated by movement of said shoulder portion; and a locking member for controlling the movement of said rocker arm control switch, said locking member having a first position allowing complete freedom of movement of said control switch, a second position preventing all movement of said control switch, and a third position preventing said control switch from activating at least one electrosurgical mode.

3. A hand control for electrosurgical electrodes, comprising:

an elongated housing for containing electrical wiring and circuit-switching means, said housing having a top surface and a bottom surface and a proximal or rear end and a distal or front end, and defining a switch seat in its top surface adjacent its distal end;

an electrosurgical blade having a proximal end in said housing and a distal end extending from said distal end of said housing;

a rocker arm control switch for activating at least two electrosurgical current modes of said electrosurgical blade, said switch having a proximal end and a distal end and being pivotably mounted in the switch seat, directly above said proximal end of the electrosurgical blade;

finger-engaging portions on said proximal and distal ends of said rocker arm control switch for pivoting said control switch in two opposite directions;

a cantilevered shoulder portion on said rocker arm control switch, said shoulder portion extending rearward within said housing from said control switch;

circuit closing means having a plurality of circuit modes, said circuit closing means being activated by movement of said shoulder portion;

a nonconductive contact support member extending lengthwise axially inside said housing adjacent said rocker and defining a vertical contact channel adjacent to said distal end;

a first resilient, conductive spring contact pinned to the top of said contact support member and aligned longitudinally thereon, said contact having a distal end defining a rectangular plunger slot, and terminating in said contact channel;

a second resilient, conductive spring contact pinned to the bottom of said support member and aligned longitudinally thereon, said contact having a distal end defining a rectangular plunger slot, and terminating in said contact channel in spaced relation to said distal end of said first spring contact;

a common current conductor blade extending lengthwise axially through the contact support member and having a proximal end extending rearward therefrom, and a distal end terminating in said contact channel adjacent said plunger slots on the proximal side thereof in spaced relation to said first and second spring contacts;

three electrical wires for carrying electrical current, a first end of each of said wires being connected respectively to said proximal ends of said first spring contact, said second spring contact, and said common current conductor blade, a second end of said wires being connected respectively to a first signal terminal, a second signal terminal and a ground terminal of a dual-mode current supply or electrosurgical generator;

a conductive electrode current conductor blade having a proximal end and a distal end, said distal end of said blade being in contact with said proximal end of said electrosurgical blade, and said proximal end of said electrode current conductor blade being between said first and second spring contacts, spaced therefrom and terminating adjacent said plunger slots on said distal side thereof; and a plunger having shoulders on its upper portion and a T-shaped tip with flanges at its lower end, said plunger extending downward from said rocker arm shoulder portion passing through said spring contact plunger slots, said plunger moving upward as said distal end of said control switch is depressed, said T-shaped tip pulling said second spring contact upward and into contact with said common current conductor blade and said electrode current conductor blade, completing an electrical circuit from said electrical power source to said electrosurgical blade, and in similar manner, as said plunger is moved downward as said proximal end of said rocker arm control switch is depreseed, said plunger shoulders push said first spring contact downward and into contact with said common current conductor blade and said electrode current conductor blade, completing an electrical circuit from said power source to said electrosurgical blade.

4. A hand control for electrosurgical electrodes, comprising:

a housing for containing electrical wiring circuits and circuit-switching means, said housing having a proximal end and a distal end, a bottom surface, and a top surface defining a switch seat adjacent its distal end;

an electrosurgical blade having a proximal end in said housing and a distal end extending from said distal end of said housing, said blade having a single sharp edge for use as a conventional surgical scalpel;

a rocker arm control switch for activating at least two electrosurgical current modes of said electrosurgical blade, said switch having a proximal end and a distal end and being pivotably mounted between said ends in said switch seat, directly above said proximal end of said electrosurgical blade;

finger-engaging portions on said proximal and distal ends of said rocker arm contact switch for pivoting said control switch in a first and a second direction;

a cantilevered shoulder portion rigidly mounted on said proximal end of said rocker arm control switch and extending proximally within the housing beyond said proximal end of said electrosurgical blade;

circuit closing means having a plurality of circuit modes, said circuit closing means being transversely mounted within said housing, between said top and bottom surfaces, rearwardly of said proximal end of said electrosurgical blade and connected to and movable with said shoulder portion to selectively activate said circuits; and a locking member for restricting the motion of said rocker arm control switch, said locking member having a first position allowing complete freedom of motion of said control switch, a second position locking the control switch motionless in a single position, and a third position preventing the control switch from activating at least one electrosurgical mode.

5. A hand control for electrosurgical electrodes, comprising:

a housing for containng electrical wiring and circuit-switching means, said housing having a proximal end and a distal end, a bottom surface, and a top surface defining a switch seat adjacent its distal end;

an electrosurgical blade having a proximal end in said housing and a distal end extending from said distal end of said housing, said blade having a single sharp edge for use as a conventional surgical scalpel;

a rocker arm control switch for activating at least two electrosurgical current modes of said electrosurgical blade, said switch having a proximal end and a distal end and being pivotably mounted in said switch seat, directly above said proximal end of said electrosurgical blade;

finger-engaging portions on said proximal and distal ends of a said rocker arm contact switch for pivoting said control switch in a first and a second direction;

a cantilevered shoulder portion on said rocker arm control switch, said shoulder portion extending proximally within said housing from said control switch;

a nonconductive contact support member extending lengthwise axially inside said housing adjacent said rocker arm control switch, said support member having a distal end and defining a vertical contact channel adjacent to said distal end;

a first resilient, conductive spring contact pinned to the top of said contact support member and aligned longitudinally thereon, said contact having a distal end defining a rectangular plunger slot, and terminating in said contact channel;

a second resilient, conductive spring contact pinned to the bottom of said support member and aligned longitudinally thereon, said contact distal end defining a rectangular plunger slot, and terminating in said contact channel in spaced relation to said distal end of said first spring contact;

a common current conductor blade extending lengthwise axially through said contact support member and having a proximal end extending rearward therefrom and a distal end terminating in said contact channel adjacent said plunger slots and on said proximal side thereof in spaced relation to said first and second spring contacts;

three electrical wires for carrying electrical current, one end of each of said wires being connected respectively to said proximal ends of said first spring contact, said second spring contact, and said common current conductor blade, and the other end of said wires being connected respectively to a first signal terminal, a second signal terminal, and a ground terminal of a dual-mode current supply or electrosurgical generator;

a conductive electrode current conductor blade having a proximal and a distal end, said distal end of said blade being in contact with said proximal end of said electrosurgical blade, and said proximal end of said electrode current conductor blade being between said first and second spring contacts, spaced therefrom and terminating adjacent said plunger slots on said distal side thereof;

a plunger having shoulders on its upper portion and a T-shaped tip with flange at its lower end, said plunger extending downward from said rocker arm shoulder portion and passing through said spring contact plunger slots, said plunger moving upward as the distal end of said control switch is depressed, the T-shaped tip pulling said second spring contact upward and into contact with said common current conductor blade and said electrode current conductor blade, completing an electrical circuit from the electrical power source to said electrosurgical blade, and in similar manner, as said plunger is moved downward as said proximal end of said rocker arm control switch is depressed, said plunger shoulders push said first spring contact downward and into contact with said common current conductor blade and said electrode current conductor blade, completing an electrical circuit from the power source to said electrosurgical blade; and a locking member for restricting the motion of said rocker arm control switch, said locking member having a first position allowing complete freedom of motion of said control switch, a second position locking said control switch motionless in a single position, and a third position allowing said control switch to move in a restricted range.

6. A hand control for electrosurgical electrodes, comprising:

a housing for containing electrical wiring and circuit-switching means, said housing having a proximal end and a distal end, a bottom surface, and a top surface defining a switch seat adjacent its distal end;

an electrosurgical blade having a proximal end in said housing and a distal end extending from said distal end of said housing, said blade having a single sharp edge for use as a conventional surgical scalpel;

a rocker arm control switch for activating at least two electrosurgical current modes of said electrosurgical blade, said switch having a proximal end and a distal end and being pivotably mounted in said switch seat, directly above said proximal end of said electrosurgical blade;

finger-engaging portions on said proximal and distal ends of a said rocker arm contact switch for pivoting said control switch in a first and a second direction;

a cantilevered shoulder portion on said rocker arm control switch, said shoulder portion extending proximally within the housing from said control switch;

circuit closing means having a plurality of circuit modes, said circuit closing means being activated by movement of said shoulder portion;

a slide locking arm having a proximal and a distal end, said arm positioned longitudinally inside said housing and with freedom to slide forward and rearward;

a slide-locking flange protruding upward from said proximal end of said locking arm;

a slide-locking thumb release groove defined by said upper surface of said housing;

a slide-locking thumb release attached to said locking arm and protruding upward therefrom, for moving said slide-locking arm forward and backward, said thumb release being free to move within said slide-locking thumb release groove;

a forked locking shoulder on said distal end of said locking arm, said locking shoulder having an upper flange and a shorter lower flange, together forming a locking recess;

a first, rear locking notch defined by said top surface of the housing, for receiving said slide-locking flange and positioning said slide-locking arm so that said slide-locking shoulder does not restrict the vertical movement of said rocker arm shoulder, allowing complete freedom of movement thereof;

a second, center locking notch defined by said top surface of the housing and located adjacent to and distally from said rear locking notch, for receiving said slide-locking flange and positioning said slide-locking arm so that said upper flange of said slide-locking shoulder restrains said rocker arm locking shoulder from moving upward a sufficient distance to complete an electrical circuit through said second spring contact to said electrosurgical blade; and a third, forward locking notch defined by said top surface of the housing and located adjacent to and distally from said center locking notch, for receiving said slide-locking arm so that said rocker arm locking shoulder is held securely in said slide-locking shoulder recess, preventing all vertical movement of said plunger, and locking the spring contacts in a neutral position with no electrical connection possible between the power source and said electrosurgical blade.

7. A hand control for electrosurgical electrodes, comprising:

a housing for containing electrical wiring and circuit closing means, said housing having a proximal and a distal end, and defining a distal socket bore for receiving an electrosurgical blade;

a top surface on said housing, said top surface defining:

a switch seat positioned above said socket bore near the distal end of said housing;

a rear locking notch located proximally from said switch seat generally in the longitudinal center of said top surface;

a center locking notch adjacent said rear locking notch and located distally therefrom;

a forward locking notch adjacent said center locking notch and located distally therefrom; and a slide-locking thumb release groove located between said switch seat and said locking notches;

an electrosurgical blade having a proximal end in said socket bore and a distal end extending from the distal end of said housing, said distal blade end having a downward hook-shaped configuration and having a single sharp edge on its top for use as a conventional scalpel;

a rocker arm control switch pivotably mounted in said switch seat, said switch having proximal and distal ends with finger-engaging portions thereon for moving the switch in a first and a second direction by finger pressure, said switch movement activating circuit closing means;

a cantilevered shoulder portion located inside the housing and extending proximally from said control switch, said shoulder portion moving vertically in an arc as said switch is moved in said first and second directions;

a nonconductive contact support member extending lengthwise axially inside said housing adjacent said rocker arm control switch, said support member having a distal end and defining a vertical contact channel adjacent to said distal end;

a first conductive, resilient spring contact pinned to the top of said contact support member and aligned longitudinally thereon, said contact positioned longitudinally inside said housing, having a distal end defining a plunger slot, and terminating in said contact channel;

a second conductive, resilient spring contact pinned to the bottom of said support member and aligned longitudinally thereon located beneath said first spring contact and spaced therefrom, said second spring contact having a distal end, said distal defining a plunger slot, and terminating in said contact channel in spaced relation to said distal end of said first spring contact;

a common current conductor blade extending lengthwise axially through the contacts support member and proximal end extending rearward therefrom, and a distal end terminating in said contact channel adjacent said plunger slots on the proximal side thereof in spaced relation to said first and second spring contacts;

a first electrical wire for carrying electrical current, having a distal end connected to the proximal end of said first spring contact and a proximal end connected to a first signal terminal of a conventional dual mode current supply or electrosugical generator;

a second electrical wire for carrying electrical current, having a distal end connected to the proximal end of said first spring contact and a proximal end connected to a second signal terminal of a conventional dual mode current supply or electrosurgical generator;

a third electrical wire for carrying electrical current, having a distal end connected to the proximal end of said common current conductor blade, and a proximal end connected to a ground terminal of a dual-mode current supply or electrosurgical generator;

a conductive electrode current conductor blade having a proximal end and a distal end, said distal end of said blade being in contact with the proximal end of the electrosurgical blade, and said proximal end of said electrode current conductor blade being between the first and second spring contacts, spaced therefrom and terminating adjacent said plunger slots on the distal side thereof;

a plunger having shoulders on its upper portion and at its lower end a T-shaped tip with flanges, said plunger extending downward from said rocker arm shoulder portion, passing through the spring contact plunger slots, said T-shaped tip moving upward as the distal end of the control switch is depressed, said tip pulling the second spring contact upward and into contact with the common current conductor blade and the electrode current conductor blade, completing an electrical circuit from the electrical power source to the electrosurgical blade, and as the proximal end of the control switch is depressed, the plunger shoulder pushing said first spring contact downward and into contact with the common current conductor blade and the electrode current conductor blade, completing an electrical circuit from the power source to the electrosurgical blade; and a locking member for controlling the movement of the rocker arm control switch, said locking member having a first position allowing complete freedom of movement of the control switch, a second position preventing all movement of the control switch, and a third position preventing the control switch from activating at least one electrosurgical current mode.

8. A hand control for electrosurgical electrodes as claimed in claim 7, wherein said locking member comprises:

a slide-locking arm having a forward and a distal end, said arm positioned longitudinally inside said housing with freedom to slide forward and rearward;

a slide-locking flange protruding upward from the proximal end of said locking arm:

a forked locking shoulder on the distal end of said slide-locking arm, said shoulder having an upper flange and a shorter lower flange, together forming a locking recess; and a slide-locking thumb release integrally molded into said locking arm and protruding upward therefrom through said slide-locking thumb release groove, said thumb release being free to slide forward and rearward in said groove and to move the slide-locking member into any of three positions:

(1) with the slide-locking flange locked into the rear locking notch, the slide-locking member is positioned so that the slide-locking shoulder does not restrict the vertical movement of the rocker arm shoulder, allowing complete freedom of movement thereof; or (2) with the slide-locking flange locked into the center locking notch, the slide-locking member is positioned so that the upper flange of the slide-locking shoulder restrains the rocker arm locking shoulder from moving upward a sufficient distance to complete an electrical circuit through the second spring contact to the electrosurgical blade; or (3) with the slide-locking flange locked into the forward locking notch, the slide-locking member is positioned so that the rocker arm locking shoulder is held securely in the slide-locking shoulder recess, preventing all vertical movement of the plunger, and locking the spring contacts in a neutral position with no electrical connection possible between the power source and the electrosurgical blade.

* * * * *